United States Patent
Radue et al.

(10) Patent No.: US 11,199,164 B2
(45) Date of Patent: *Dec. 14, 2021

(54) ELECTRONIC FUEL INJECTION SYSTEM AND METHOD FOR ENGINES

(71) Applicant: Kohler Co., Kohler, WI (US)

(72) Inventors: Martin L. Radue, Plymouth, WI (US); Michael Kleczewski, Cleveland, WI (US)

(73) Assignee: KOHLER CO., Kohler, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/901,105

(22) Filed: Jun. 15, 2020

(65) Prior Publication Data

US 2020/0309759 A1 Oct. 1, 2020

Related U.S. Application Data

(60) Division of application No. 16/404,880, filed on May 7, 2019, now Pat. No. 10,725,015, which is a
(Continued)

(51) Int. Cl.
*F02M 35/09* (2006.01)
*B01D 46/00* (2006.01)
(Continued)

(52) U.S. Cl.
CPC ......... *F02M 35/09* (2013.01); *B01D 46/0086* (2013.01); *F01M 2011/14* (2013.01); *F01M 2011/142* (2013.01); *F01M 2011/1406* (2013.01); *F01M 2011/1413* (2013.01); *F01M 2011/1426* (2013.01); *F01M 2011/1433* (2013.01); *F01M 2011/1466* (2013.01); *F01M 2011/1473* (2013.01); *F01M 2011/1486* (2013.01); *F02D 41/26* (2013.01);
(Continued)

(58) Field of Classification Search
CPC .......... B01D 46/0086; F02M 35/0205; F02M 35/0207; F02M 35/0208; F02M 35/08; F02M 35/09
See application file for complete search history.

(56) References Cited

U.S. PATENT DOCUMENTS 4,847,768 A 7/1989 Schwartz et al.
5,555,500 A 9/1996 Ogawa et al.
(Continued)

FOREIGN PATENT DOCUMENTS

| | | |
|---|---|---|
| EP | 0489261 A2 | 10/1992 |
| FR | 3021112 A1 | 11/2015 |
| JP | 2008289220 A | 11/2008 |

OTHER PUBLICATIONS

Chinese Office Action for Chinese Application No. 201780012225.0 dated Jul. 9, 2020, 4 pages.
(Continued)

*Primary Examiner* — Kevin R Steckbauer
(74) *Attorney, Agent, or Firm* — Klintworth & Rozenblat IP LLP

(57) ABSTRACT

A system includes an electronic fuel injection system of an engine, the electronic fuel injection system including an electronic governor control unit for controlling various functions of the engine.

16 Claims, 6 Drawing Sheets

Related U.S. Application Data continuation of application No. 15/441,913, filed on Feb. 24, 2017, now Pat. No. 10,323,597.

(60) Provisional application No. 62/299,885, filed on Feb. 25, 2016.

(51) Int. Cl.
  *F02D 41/26* (2006.01)
  *F02D 41/22* (2006.01)
  *G01N 33/28* (2006.01)
  *F01M 11/10* (2006.01)

(52) U.S. Cl.
  CPC .................. *F02D 2041/228* (2013.01); *F02D 2200/0404* (2013.01); *F02D 2200/0406* (2013.01); *G01N 33/2888* (2013.01)

(56) References Cited

U.S. PATENT DOCUMENTS

| | | | |
|---|---|---|---|
| 5,561,600 A | 10/1996 | McCombie | |
| 5,633,796 A | 5/1997 | Cullen et al. | |
| 5,831,154 A | 11/1998 | Guertler et al. | |
| 5,914,890 A | 6/1999 | Sarangapani et al. | |
| 6,253,601 B1 | 7/2001 | Wang et al. | |
| 6,449,538 B1 | 9/2002 | Kubo et al. | |
| 6,711,525 B1 | 3/2004 | Fox et al. | |
| 7,032,573 B2 * | 4/2006 | Ardisana | F02D 41/18 123/198 E |
| 7,441,449 B2 * | 10/2008 | Wang | F02D 35/0023 73/114.31 |
| 7,441,450 B2 * | 10/2008 | Lain | F02D 41/22 73/114.37 |
| 7,444,234 B2 * | 10/2008 | Bauerle | F02M 35/09 701/114 |
| 7,591,173 B2 * | 9/2009 | Benscoter | B01D 46/0086 73/114.33 |
| 8,701,473 B2 * | 4/2014 | Uehara | F02M 35/09 73/114.31 |
| 9,869,665 B2 | 1/2018 | Chapman, III | |
| 9,983,114 B2 * | 5/2018 | Henderson | B01D 46/0086 |
| 10,100,790 B1 * | 10/2018 | Xiao | F02B 39/10 |
| 10,302,325 B1 * | 5/2019 | Osborne | F24F 11/30 |
| 10,854,065 B1 * | 12/2020 | Pan | G08B 21/182 |
| 2002/0133274 A1 | 9/2002 | Kubo | |
| 2005/0240338 A1 * | 10/2005 | Ardisana | F02D 41/18 701/114 |
| 2008/0178842 A1 * | 7/2008 | Lain | F02D 41/0002 123/434 |
| 2008/0183366 A1 * | 7/2008 | Bauerle | F02M 35/09 701/103 |
| 2008/0223123 A1 * | 9/2008 | Wang | F02D 35/0023 73/114.31 |
| 2008/0229720 A1 * | 9/2008 | Benscoter | B01D 46/0086 55/290 |
| 2009/0234533 A1 | 9/2009 | Trinkner | |
| 2012/0042717 A1 | 2/2012 | Schneider et al. | |
| 2013/0036804 A1 * | 2/2013 | Uehara | F02M 35/09 73/114.31 |
| 2015/0192560 A1 | 7/2015 | Basu et al. | |
| 2015/0330857 A1 * | 11/2015 | Henderson | F02M 35/09 702/35 |
| 2015/0338386 A1 | 11/2015 | Chapman, III | |
| 2017/0043290 A1 | 2/2017 | Segard | |
| 2018/0023523 A1 * | 1/2018 | Jammoussi | F02M 35/09 701/31.5 |
| 2018/0229744 A1 | 8/2018 | Manzari et al. | |
| 2018/0246010 A1 | 8/2018 | Bachmann et al. | |
| 2018/0266354 A1 * | 9/2018 | Landolsi | F02D 41/18 |

OTHER PUBLICATIONS

Bommareddi, A. "An Engine Oil Life Algorithm, A Thesis in Mechanical Engineering," Pennsylvania State University 2009, 103 pages.
International Search Report and Written Opinion for International Patent Application No. PCT/US2017/019385 dated Jul. 10, 2017, 20 pages.
English Summary of Chinese Office Action for Application No. 201780012225.0 dated Dec. 30, 2019, 2 pages.
Chinese Office Action for Chinese Application No. 201780012225.0 dated Dec. 30, 2019, 7 pages.

* cited by examiner

ELECTRONIC FUEL INJECTION SYSTEM AND METHOD FOR ENGINES

CROSS REFERENCE TO RELATED APPLICATION

This application is a divisional of co-pending U.S. application Ser. No. 16/404,880, which was filed on May 7, 2019, which is a continuation of issued U.S. Pat. No. 10,323,597, which was issued on Jun. 18, 2019 and claims priority benefit from U.S. Provisional Application Ser. No. 62/299,885, which was filed on Feb. 25, 2016, which is incorporated by reference in its entirety.

BACKGROUND

Fuel injection is a system for introducing fuel into internal combustion engines.

SUMMARY

According to one aspect, systems and methods include an electronic fuel injection system of an engine, the electronic fuel injection system including an electronic governor control unit for one or more of oil health tracking, monitoring air cleaner health, throttle position auto learning, etc.

Other systems, methods, features, and advantages is or will become apparent upon examination of the following figures and detailed description. It is intended that all such additional systems, methods, features, and advantages be included within this description and be protected by the accompanying claims.

BRIEF DESCRIPTION OF THE DRAWINGS

In association with the following detailed description, reference is made to the accompanying drawings, where like numerals in different figures can refer to the same element. The features of the drawings are not necessarily drawn to scale.

DETAILED DESCRIPTION

Figure 1:
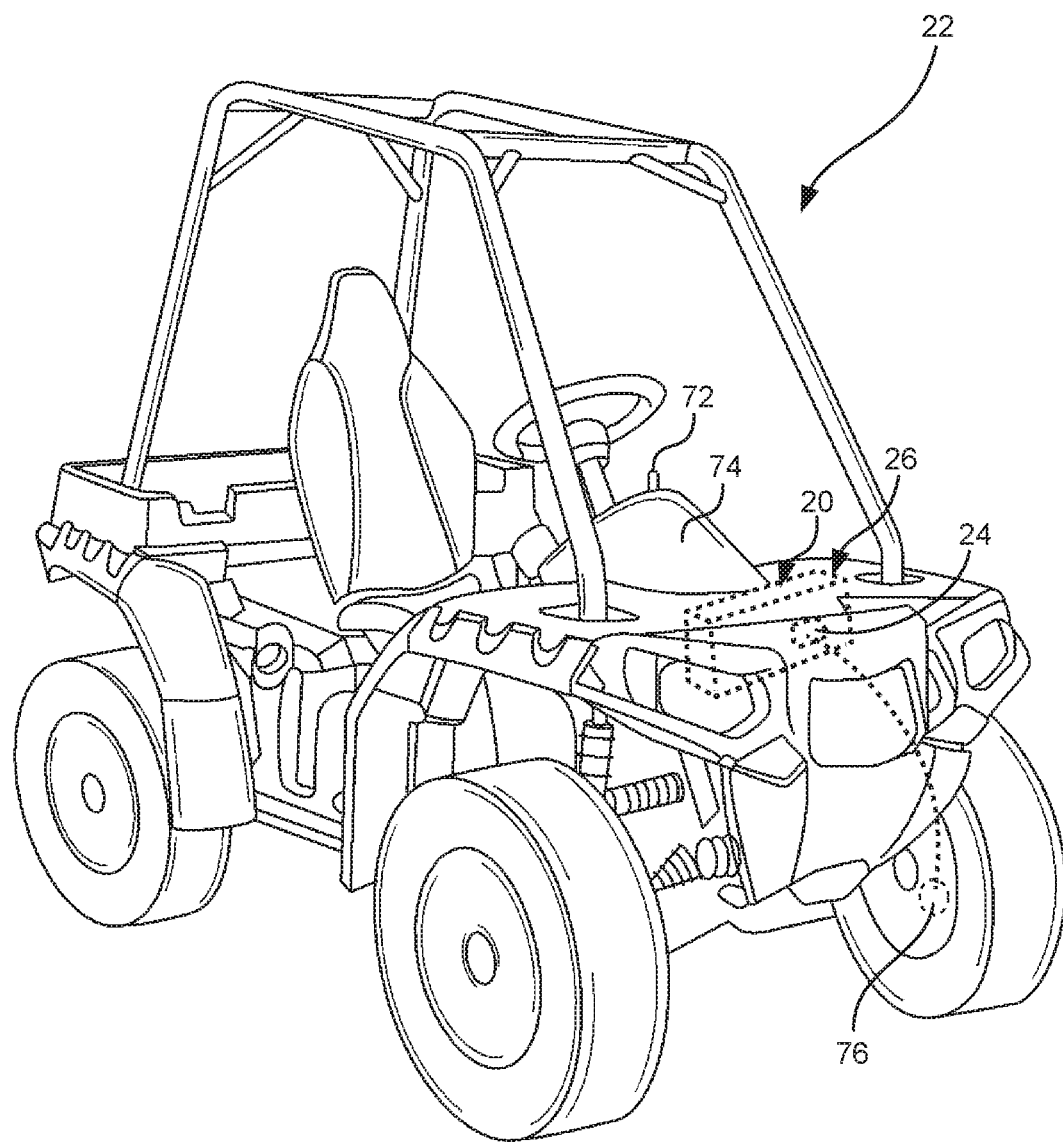
FIG. 1 is a perspective view of an example vehicle.

While the disclosure may be susceptible to embodiment in different forms, there is shown in the drawings, and herein is described in detail, a specific embodiment with the understanding that the present disclosure is to be considered an exemplification of the principles of the disclosure, and is not intended to limit the disclosure to that as illustrated and described herein. Therefore, unless otherwise noted, features disclosed herein may be combined together to form additional combinations that were not otherwise shown for purposes of brevity. It is further appreciated that in some embodiments, one or more elements illustrated by way of example in a drawing(s) may be eliminated and/or substituted with alternative elements within the scope of the disclosure.

FIG. 1 is a perspective view of an example vehicle 22. An engine 20 for the vehicle 22 is provided which may have an electronic governor control unit (EGU) 24 to execute determined functionalities of the engine 20 and/or vehicle 22, e.g., described herein. The engine 20 can also be used for non-vehicle applications, including, but not limited to, welders, power washers, mowers, generators, etc. For the sake of explanation, the EGU 24 is referenced, but any type of control unit, processor, microprocessor, etc., or combination thereof, with or without an electronic governor component, can be used to execute the functions described herein. In some examples, the EGU 24 may be embedded into, or separate from but connected with, an electronic fuel injection (EFI) system 26. In some examples, the engine 20 includes a Kohler Command V-Twin engine, though many other engines are possible. Systems, methods and/or logic related to the EGU 24 are described herein.

Figure 2:
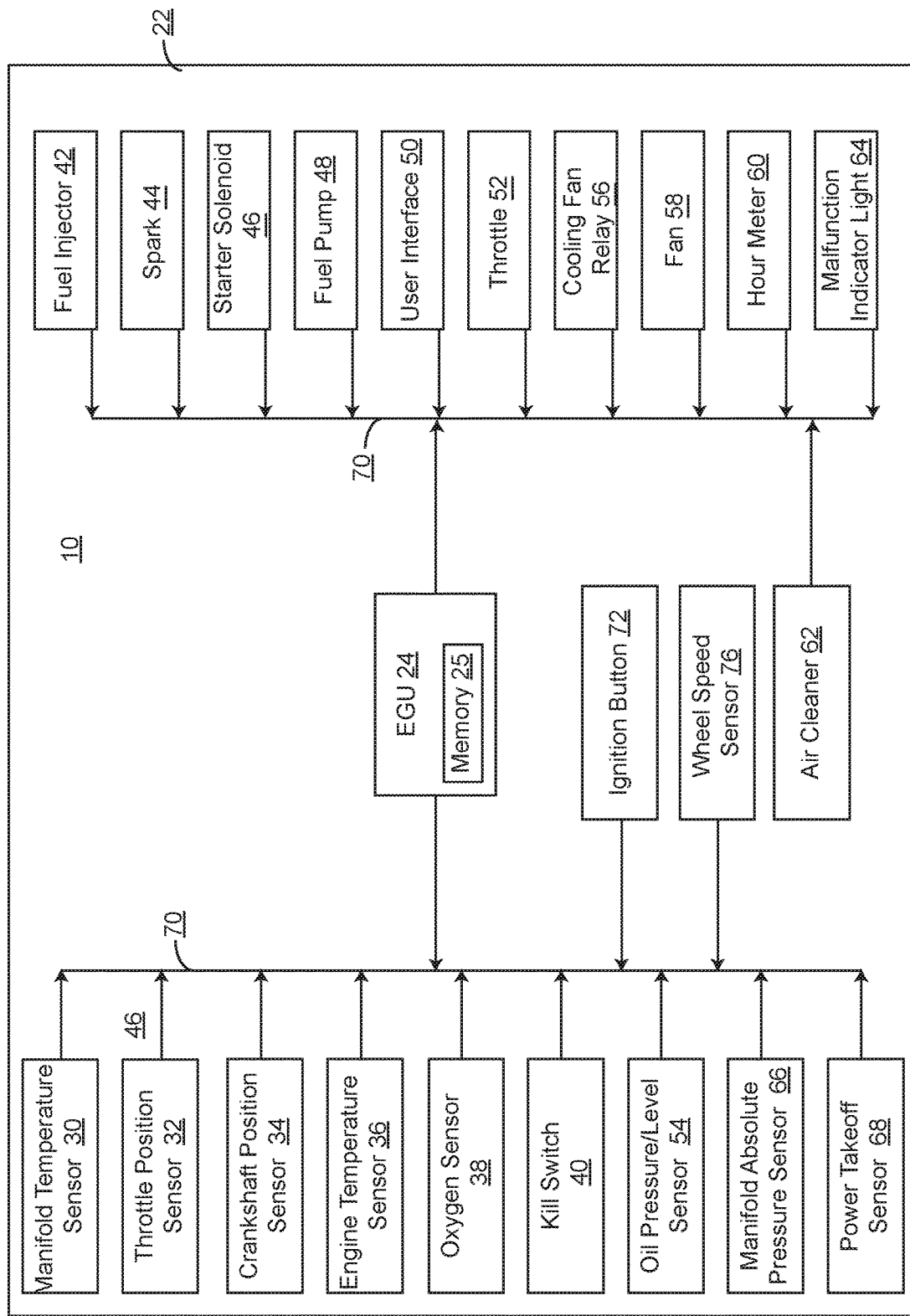
FIG. 2 is a block diagram of an example control system of the vehicle.

FIG. 2 is a block diagram of an example control system 10 of the vehicle 22. The control system 10 can include the EGU 24 and associated wiring and/or controller area network (CAN) bus 70, and other supporting elements of the EGU 24, including, but not limited to, one or more temperature sensor 30, manifold air pressure sensor 66, throttle position sensor 32, crankshaft position sensor 34, engine temperature sensor 36, oxygen sensor 38, kill switch 40, the oil pressure switch or oil level switch 54, etc. In some examples, the control system 10 can send signals 46 to be received and processed by the EGU 24, where the signals 46 represent various sensed and/or switch information, e.g., air temperature and volume, throttle position, engine speed, engine temperature, oxygen information for closed loop control, and engine activation, etc.

The EGU 24 may be configured to perform many of the functions for the vehicle 22 and/or the engine 20, for example as described herein. To execute the functions, the EGU 24 may include an integrated memory 25, and/or be connected with memory, that can store instructions (e.g., compiled executable program instructions, un-compiled program code, some combination thereof, or the like)), which when performed (e.g., executed, translated, interpreted, and/or the like) by the EGU 24, causes the EGU 24 to perform the functions, logic and other processes described herein.

For example, the EGU 24 can process the input signals 46 and output control signals to fuel injectors 42 and spark units 44, etc. e.g., based on information from the input signals 46. In one example, by monitoring engine running speed, e.g., determined from the crankshaft position sensor 34, the EGU 24 can send control signals to fuel injector 42 and spark units 44, or other components such as servo motor ignition coils and ignition modules with individual built-in drivers, etc., to control operation of those components. The EGU 24 can also interface with other components of the vehicle 22, including, but not limited to, an ignition button 72, kill switch 40 and starter solenoid 46. The ignition button 72 and kill switch 40 can be positioned on the dashboard 74 of the vehicle 22. The starter solenoid 46 can receive a start signal from the EGU 24 to start the engine 20 based on information received from the start button 72, and while the kill switch 40 is open. The kill switch 40 can send signals to the EGU 24 to stop the engine 20 from operating, e.g., when the kill switch 40 is closed. In some examples, the kill switch 40 connects with the starter solenoid 46 and to circuit ground via the wiring and/or controller area network (CAN) bus 70 to prevent signals from reaching starter solenoid 46, and/or the EGY 24 can prevent a fuel pump 48 from sending fuel to the engine 20.

The EGU 24 can be configured to allow an operator to start the engine 20 locally or remotely from the engine 20. For example, the user may push or otherwise actuate a wired ignition button 72 positioned on the dashboard 74 of the vehicle 22 to send a voltage signal to the EGU 24 indicating the ignition button 72 has been pressed. The EGU 24 can then send a control signal to the starter solenoid 46 to start the engine. Additionally, the operator may actuate an ignition button on a fob or a "Start" indicator on another device such as a smart phone or personal computer located remotely from the vehicle 20, e.g., wirelessly, to send a controller area network (CAN) message, logic request, or other message or signal to the EGU 24 to indicate a start. In some examples, the wired ignition button 72, fob, and/or other remote device may be configured to provide a Request to Start (RTS) signal (the voltage signal, the CAN message, or other message or signal) to the EGU 24 upon actuation. The EGU 24 may process the signal to start the engine 20 when the EGU 24 receives the RTS, e.g., by sending a control signal to the starter solenoid 46 located on the engine 20. The EGU 24 can also output a start confirmed signal (SCS) signal to an audio and/or visual device, e.g., horn, lamp, dash panel display, and/or other user interface 50, e.g., located on the dashboard 74 of the vehicle 22 and/or on the engine 20 itself, to warn/inform a user of an expectant start of the engine 20. To achieve this, in some implementations, four pins can be allocated on the EGU 24 for the analog version, and two output pins can be used for the CAN bus 70 version of the wiring.

In the analog version, a first pin of the EGU 24 can be used to receive the request to start (RTS) signal which includes a 5 or 12 V continuous/momentary signal activated when the operator requests the start. The EGU 24 can use a second pin to send signals to the starter solenoid 46 to activate the starter solenoid 46 via low side drive of the start relay. The EGU 24 can use a third pin to output the start confirmed signal (SCS) to the horn, lamp, dash panel display, and/or other user interface 50, etc., e.g., located on the dashboard 74 of the vehicle 22 or the engine 20. For example, the horn or lamp can inform a welder performing welds remote from the engine who may not hear the engine running. In some examples, the EGU 24 disengages the starter after the start confirmation (e.g., based on a signal from the crankshaft position sensor 34 received by the EGU 24 to determine engine speed), to avoid trying to start the engine 20 after the engine 20 is already running. The crankshaft position sensor 34 can be located at an outer diameter of a flywheel. The EGU 24 can use a fourth pin to warn/inform a local user of imminent start of the engine 20 via voltage to horn, lamp, dash panel display, and/or other user interface 50, e.g., located on the dashboard 74 of the vehicle 22 or the engine 20.

In the CAN bus 70 messaging version, the EGU 24 can use the CAN bus 70 to send messages signifying the RTS and the SCS. The EGU 24 can use the first pin to activate the starter solenoid 46 via low side drive of the start relay. The EGU 24 can use the second pin to warn/inform the user of imminent start via voltage to horn, lamp, dash panel display, and/or other user interface 50, e.g., located on the dashboard 74 of the vehicle 22 or the engine 20. The EGU 24 can inactivate the remote start feature when the key switch for ignition is off.

In some examples, the EGU 24 can perform speed limit functions for the vehicle 22. The EGU 24 receives a 5 V or 12 V input square wave Vehicle Speed Signal (VSS), e.g., via wheel speed sensor 76 located on a wheel of the vehicle 22, and outputs commands to limit the opening of the throttle 52 after the vehicle 22 reaches the determined speed limit. The determined speed limit can be stored in memory 25. The EGU 24 monitors the VSS and controls the speed of the vehicle 22 according to the determined vehicle speed limit. Therefore, the EGU 24 can be used for the applications (e.g., utility vehicles) whose speed is controlled. In some example, the EGU 24 can process the speed indicated by the VSS into engineering units.

In some examples, the EGU 24 limits the throttle opening once the vehicle 22 reaches the speed limit and uses three pins to achieve this purpose. The EGU 24 can have two pins dedicated to receive Vehicle Speed Signal (VSS), e.g., received from the wheel speed sensor 76 located on the vehicle 22. The EGU 24 can receive the VSS as a 5 or 12 V square wave signal, or any sensor signal which is scaled by calibration parameter to act as vehicle speed in desired engineering units, e.g., miles per hour (MPH). The EGU 24 uses the third pin which can be pulled up to 12 V to differentiate between two speed settings, each represented by a discrete variable, e.g., maximum speed and speed at which the EGU 24 stops controlling the opening of the throttle 52 to slow the vehicle 22. In some examples, the EGU 24 controls the throttle 52 to stop opening after the vehicle 22 reaches the determined speed limit, and stops controlling the throttle opening thereafter when the speed goes below a determined threshold. The speed thresholds can be stored in memory 25.

Figure 3:
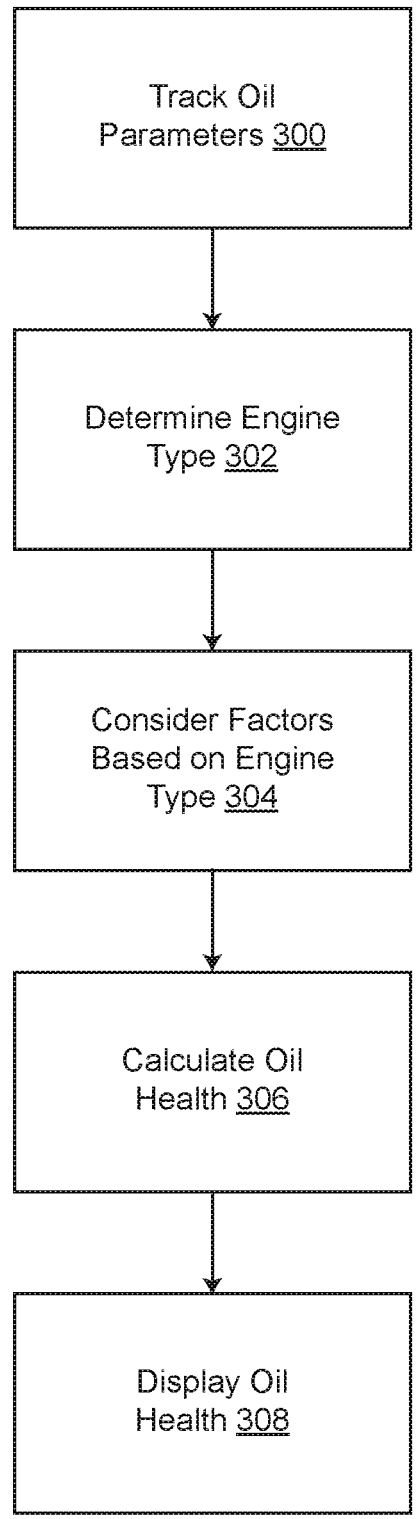
FIG. 3 is a flowchart of an example oil health tracking.

FIG. 3 is a flowchart of an example oil health tracking by the EGU 24. The EGU 24 may execute oil health/hours processes to track and display an indication of a health of the oil of the engine 20 (300). In some examples, the EGU 24 can estimate oil health in an air cooled engine by knowing the run time hours since last oil change, the engine rpm and load profile, the engine operating temperatures, the average engine run time, and the number of starts of the engine 20 (302). The EGU 24 can track the information and develop correlations for the health of the oil. A variable representing a typical oil life span, e.g., in hours of engine run time, may be stored in the calibration layer of the EGU 24 (304). The EGU 24 may calculate the oil life used in hours, and subtract this from the stored oil life variable (306). The EGU 24 can display two or more indicators of oil life available to customers (308). Through a service tool plugged into the EGU 24, or via the CAN bus 70 on user interface 50, an "hours to oil change" may be available for display from the EGU 24. When the oil life hours reach zero, the EGU 24 can flash the malfunction indicator light (MIL) 64 at a low frequency. The MIL 64 can be located in a visible area of the engine 20, e.g., near an access point for replacing the oil. The EGU 24 can reset the life of the tracked oil health, e.g., when the old oil is replaced with new oil. One way is through the service software/CAN interface, the other is a jumper wire reset process, e.g., only using a single key cycle to reset this single parameter, avoiding a complete system reset.

In one implementation, to calculate the oil change based on measured inputs for liquid cooled engines, the EGU 24 can use the following parameters: Oil temperature—operating at oil temps below 80 or above 130 degrees C. shortens oil life; Load factor—operating above 70% load shortens oil life; Speed factor—four engine RPM categories can be defined; Cranking factor; Oil age factor—total age of oil; Dirty environment factor. With regard to an air cooled engine 20, an oil temperature model can be similar to the liquid cooled engine. The EGU 24 can consider a load factor with more resolution—the engine 20 is typically operating in a wider range of equipment and running a higher duty cycle than for liquid cooled engines. The EGU 24 can consider a speed factor—with the speed governed engine 20 expecting a narrower variation in RPM versus liquid cooled engines. The EGU 24 can consider a crank factor—characterize crank/starting effects by calculating cranks/hour. In some examples, this can assume one crank for each session, so this becomes one over the run time of that session. The EGU 24 can consider the oil age. If no real-time clock is available to the EGU 24, the EGU 24 can track oil age externally through fleet management applications. The EGU 24 can also be programmed with how dirty the environment is expected to be based on an application of the engine 20, e.g., vehicle 22, welder, power washer, generator, etc.

The EGU 24 can calculate oil health on a fixed interval time loop for oil health tracking. The time loop can be stored in memory 25 as a calibration variable with an example default variable of about 30 seconds. A two dimensional table can be stored in memory 25 to capture speed and load effects on oil life, e.g., based on inputs to the EGU 24 received from the wheel speed sensor 76 and manifold air pressure sensor 66, etc. The manifold air pressure sensor 66 can be located in the intake tract/manifold or in the throttle body of the engine 20. The factors in the table can be adjusted to characterize the speed and load effects on oil life. A one dimensional table can be stored in memory 25 to characterize the temperature effects on oil life, e.g., as inputted from the manifold temperature sensor 30. The manifold air temperature sensor 30 can be located in the manifold, e.g., to record the temperature in the manifold air stream or in the throttle body. While the engine 20 is in a run session, each time the EGU 24 puts the calculation through a loop, the EGU 24 can receive the speed/load factor and the temperature factor, multiply them together and add it to the session buffer in memory 25. The buffer can average this factor over the entire session. At the end of a run session, e.g., triggered by the switched engine power turning off, the EGU 24 can take the run session time and calculate the number of starts per hour. The EGU 24 calculated starts per hour can be processed through an exponential equation to calculate an additional oil life factor, e.g., $=0.3211*EXP(0.3624*(Starts/hr.))$.

The starts/hour factor can be multiplied to the average Speed/Load/Temp factor from the session. The overall session factor can be multiplied to the actual run time of the session to calculate an oil-hours used time. This time can be accumulated in an oil-hours used buffer in memory 25. When this buffer reaches the calibrated oil-life hours calibration, the EGU 24 can communicate an oil health message to the operator. This communication can be flashing the MIL 64 and/or a message across the CAN bus 70. The EGU 24 can be capable of some basic self-diagnostics and able to flash a MIL 64 or transmit active powertrain codes to service software.

Figure 4:
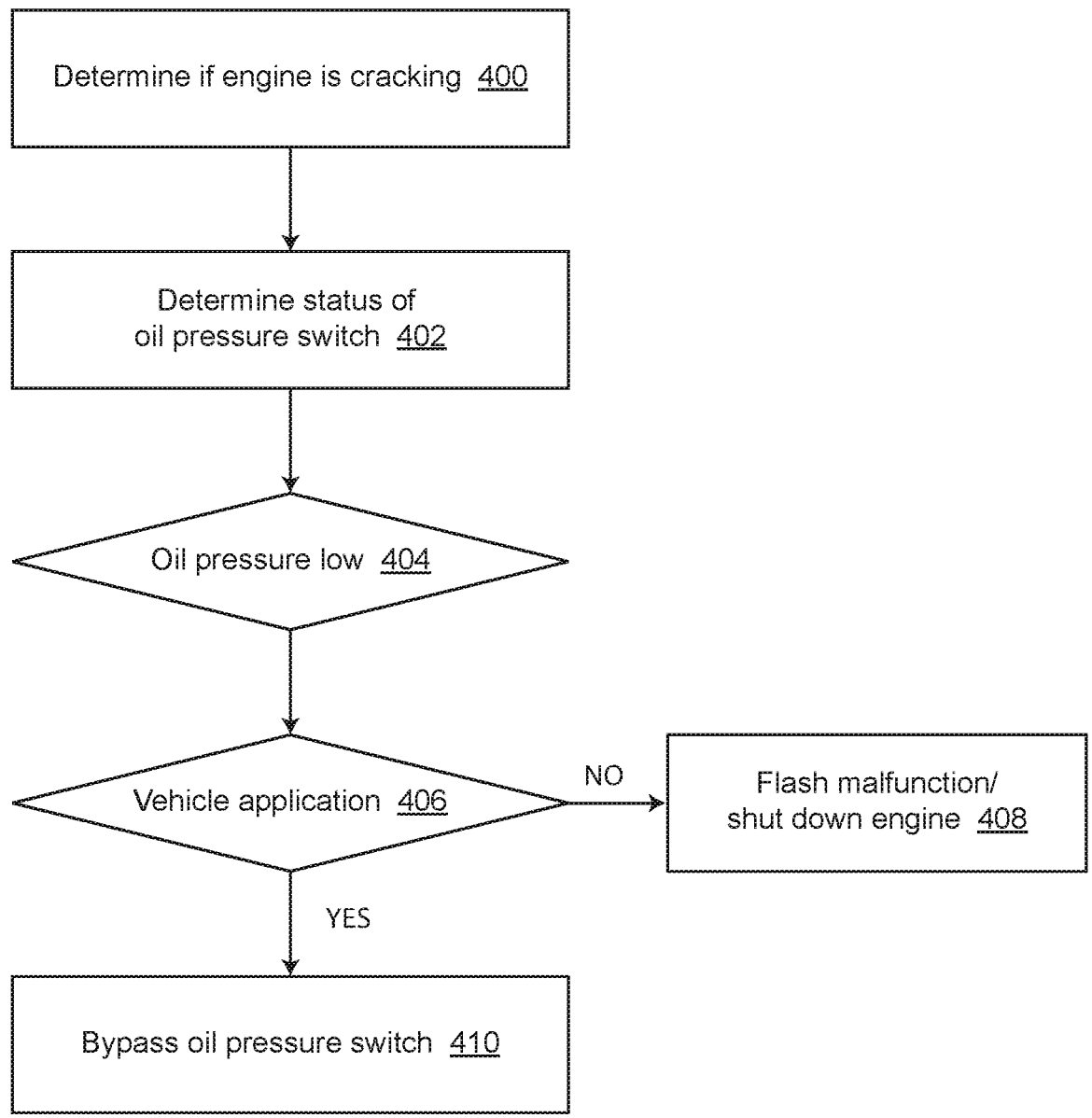
FIG. 4 is a flowchart of an example oil pressure switch control.

FIG. 4 is a flowchart of an example oil pressure/level switch control of the EGU 24. The EGU 24 receives an input 12 volt signal up to 0.25 amps from the oil pressure switch or oil level switch 54. The oil pressure/level switch 54 can be located on the side of the crankcase in communication with the pressurized oil system for oil pressure and inside the crankcase for oil level. The EGU 24 outputs an engine control signal to the engine 20 to control the engine 20 depending upon the oil pressure or oil level switch status. Based on oil pressure switch logic of the EGU 24, if the engine state is: a) cranking the EGU 24 ignores the pressure low signal from oil pressure switch 54; or b) running and pressure indicated low: the EGU 24 limits the throttle opening, or shuts the engine 20 down. Also the EGU 24 sends a low oil pressure warning out to the user interface 50 for displaying. Based on level switch logic of the EGU 24, if the engine state is: a) cranking, the EGU 24 does not allow the engine 20 to start, and send low oil warning out to the user interface 50 for displaying; b) running and level indicated low, the EGU 24 limits the throttle opening, or shuts down the engine 20. The EGU 24, also sends low oil pressure warning to the user interface 50 for displaying the low oil pressure.

EGU 24 output options include, but are not limited to, disabling start of the engine 20, limited throttle opening, and/or engine 20 shutdown, etc. configurable in a calibration layer of the EGU 24. The EGU 24 logic options include, but are not limited to, normally open or normally closed input signals, signal filtering to avoid false triggers, action delay time, and starting bypass option with calibratable delay. The EGU 24 has the option to flash a malfunction indicator light (MIL) at a high frequency and generate a CAN fault message for sending to the user interface 50 to display the malfunction.

The engine 20 with pressure lube uses signals sent from oil pressure switches (or sensors) 54 to the EGU 24 for the EGU 24 to control the engine 20 depending on the oil pressure or level switches 54 with splash lube. During engine 20 cranking (400) if the oil pressure fails to rise to the desired level of revolutions per minute (RPM), then the EGU 24 allows the momentary bypass of the oil pressure switch 54 when the electric starter is engaged so that the engine 20 can start. The EGU 24 is wired to the oil pressure switch 54 via the wiring and/or controller area network (CAN) bus 70 to monitor the oil pressure switch 54 (e.g., open and closed states) during engine 20 run case (402) and if the oil pressure is low (e.g., oil pressure switch is open) (404) responds according to Case 1 or Case 2 based on the vehicle application (406) as follows: Case 1: On non-vehicle applications, the EGU 24 triggers a malfunction code, flashes a malfunction indicator light and shuts down the engine 20 (408). Case 2: On vehicle applications (UV's), the EGU 24 triggers a malfunction code, flashes the malfunction indicator light, bypasses the oil pressure switch 54 and reduces the power output, e.g., by limiting the throttle opening giving the operator a chance to safely turn off the engine 20 (410). The throttle limit can be a single variable available in the calibration layer of the EGU 24.

The EGU 24 can have a pin available and logic stored in the memory 25 to drive a cooling fan relay 56. The logic can include two discrete temperature thresholds, e.g., a high temperature threshold indicating when to control the fan 58 and a low temperature threshold indicating when to stop controlling the fan 58, e.g., to prevent dithering. The engine temperature sensor 36 can be located at one or more positions on the engine 20, e.g., depending on packaging requirements of the engine 20, e.g., in the hot coolant passage, e.g., at the manifold, leaving the engine 20 on a liquid cooled engine, in the oil system, on the cylinder head of the engine 20, and/or in the crankcase on an air cooled engine 20. In one implementation, the EGU 24 sends a control signal to a fan 58 to turn on the fan 58 when the engine temperature sensor 36 senses about 93 C or higher. The EGU 24 keeps the fan 58 on until engine temperature goes to about 80 C or lower. Therefore, the first temperature threshold triggers the start of the fan 58 when the first temperature is reached, and when the second temperature threshold is reached and the fan 58 is operating the EGU 24 turns off the fan 58 by sending another control signal to the fan 58.

A variable stored in memory 25 for the EGU 24 to control open loop operation, e.g., ignoring the oxygen sensor 38 feedback, can include a three dimensional table with axis of RPM and TPS. The oxygen sensor 38 can be located in an engine exhaust head pipe or in the body of a muffler. The table is populated with a state value, e.g., 0, to represent open loop operation and 1 to represent a closed loop stoic (CLS) operation. The EGU 24 control can allow triggering steady fuel delivery windows at light loads, which can enhance governing stability. The TPS hysteresis value remains as a single variable and applies only when going from open loop operation to CLS operation. The EGU 24 can divide open loop operation into two distinct versions, one with oxygen feedback oversight and one without. Zero (0) can represent normal open loop operation with O2 safety oversight and correction for lean conditions. Two (2) can be used to distinguish open loop operation with no O2 oversight or correction of lean operation. Other variables can be used. The throttle angle can trigger open loop (below a determined throttle angle) and closed loop (above a determined throttle angle) operation, as determined by the EGU 24 with information from the TPS. A third mode, open loop with no oversight and correction, can occur at a determined throttle angle window between the open loop and closed loop modes.

The EGU 24 can include a logical trigger to turn on and/or utilize a second oxygen sensor 38, e.g., an oxygen sensor 38 per each engine cylinder. The EGU 24 in normal mode receives a signal sent from a single oxygen sensor 38. In dual sensor mode, each of the two cylinders can have its own oxygen sensor 38, control, and long term fuel trim correction controlled by the EGU 24. Two oxygen sensors 38 enable fuel trimming/correction specific to each cylinder rather than an average. If one cylinder is a little lean and the other is a little rich, the EGU 24 can dial each in with higher accuracy, e.g., by sending a control signal to fuel injector control 42. A value for long term fuel trim can be learned during closed loop control, e.g., if the value is 0.97 then the EGU 24 has learned to remove 3% injector pulse width from the calibration at this operating condition.

The EGU 24 can include a one dimensional table that represents the maximum allowed throttle opening over the range of operating RPM of the engine 20. The EGU 24 determines a relationship between the zero throttle point and a current position of the throttle, e.g., as received from the throttle position sensor 32. The throttle position sensor 32 can be located on the throttle shaft/throttle valve/throttle body. Generally the EGU 24 may allow the throttle to provide 100% power, but in some cases power is limited, e.g., based on an engine model stored in memory 25, by electronically limiting how far the throttle opens, e.g., about 70% or other determined value. The electronic engine power/torque control of the EGU 24 can replace, or be in addition to, a mechanical pin for controlling maximum power.

Figure 5:
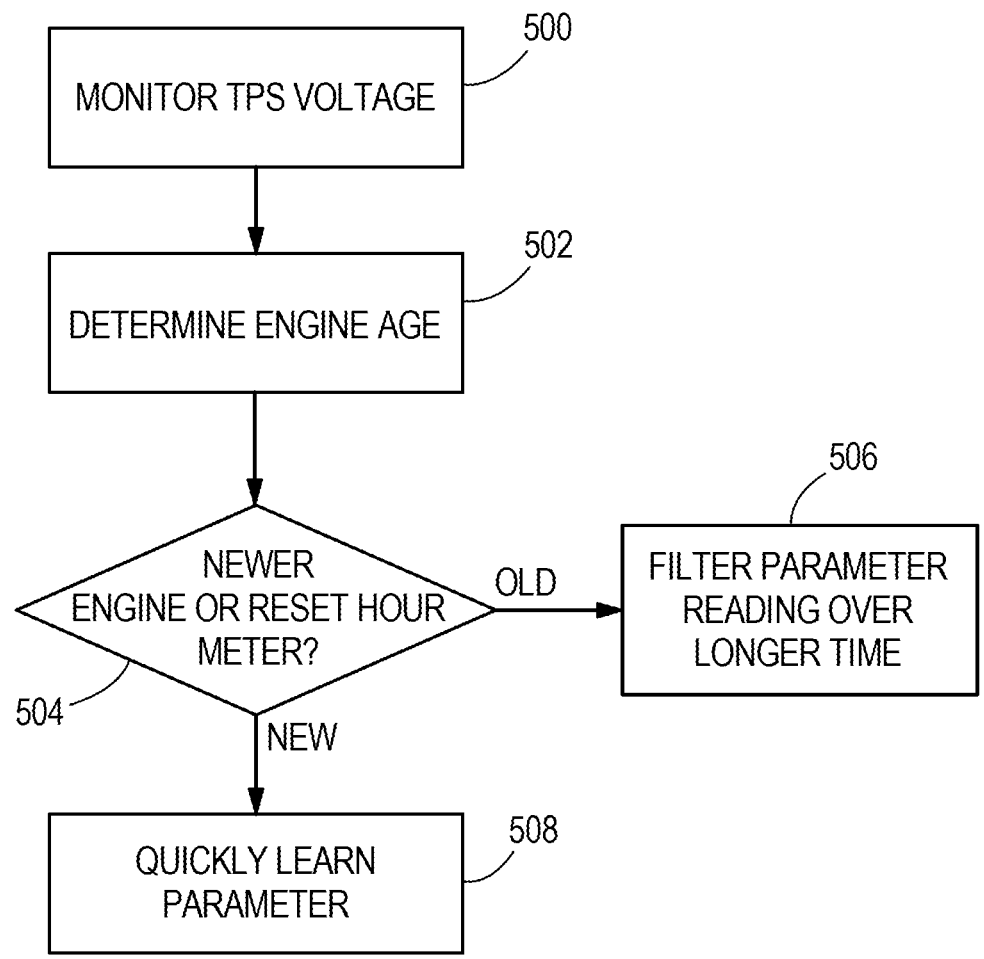
FIG. 5 is a flowchart of an example throttle position sensor auto-learn procedure.

FIG. 5 is a flowchart of an example throttle position sensor (TPS) auto-learn procedure by the EGU 24. The EGU 24 can monitor the TPS voltage signal sent by the throttle position sensor 32, e.g., the signal representing the position of the throttle 52, and save the lowest measured value assigning this to zero percent throttle, e.g., by comparing the measured voltage to the current lowest saved voltage (500). The EGU 24 can monitor the voltage from the throttle position sensor 32 continuously or periodically, e.g., every calculation software loop, or other high rate. The EGU 24 may also monitor the engine age via an hour meter 60 (502). When a system reset is done on the engine 20 the EGU 24 can reset the throttle position relationship to a determined value available in the calibration layer of the EGU 24.

As the engine 20 gets older there may be interruptions to the voltage signal, e.g., as contacts become corroded. To avoid voltage spikes from corrupting the lowest measured value, the EGU 24 may provide a calibratable variable for damping based on the engine age being newer or older (504). For example, as the engine 20 gets older, the EGU 24 may compare the measured voltage over a longer period (such as an average of about every 30 to 100 reading (506)), instead of every reading when the engine is new (508). A digital and/or analog filter included in, or connected with the EGU 24 can be used to remove unwanted voltage spikes. Variable damping can be tied to the resettable hour meter, allowing the EGU 24 to learn this lowest measured value parameter quickly when the engine 20 is new, and this value hardens over time. If there is a change to the throttle position sensor or the throttle position is adjusted during maintenance, etc., the EGU 24 can reset the hour meter 60 to have the EGU 24 quickly obtain the lowest measured value, even for an older engine 20. This can eliminate corruption of the signal that may happen over time.

Figure 6:
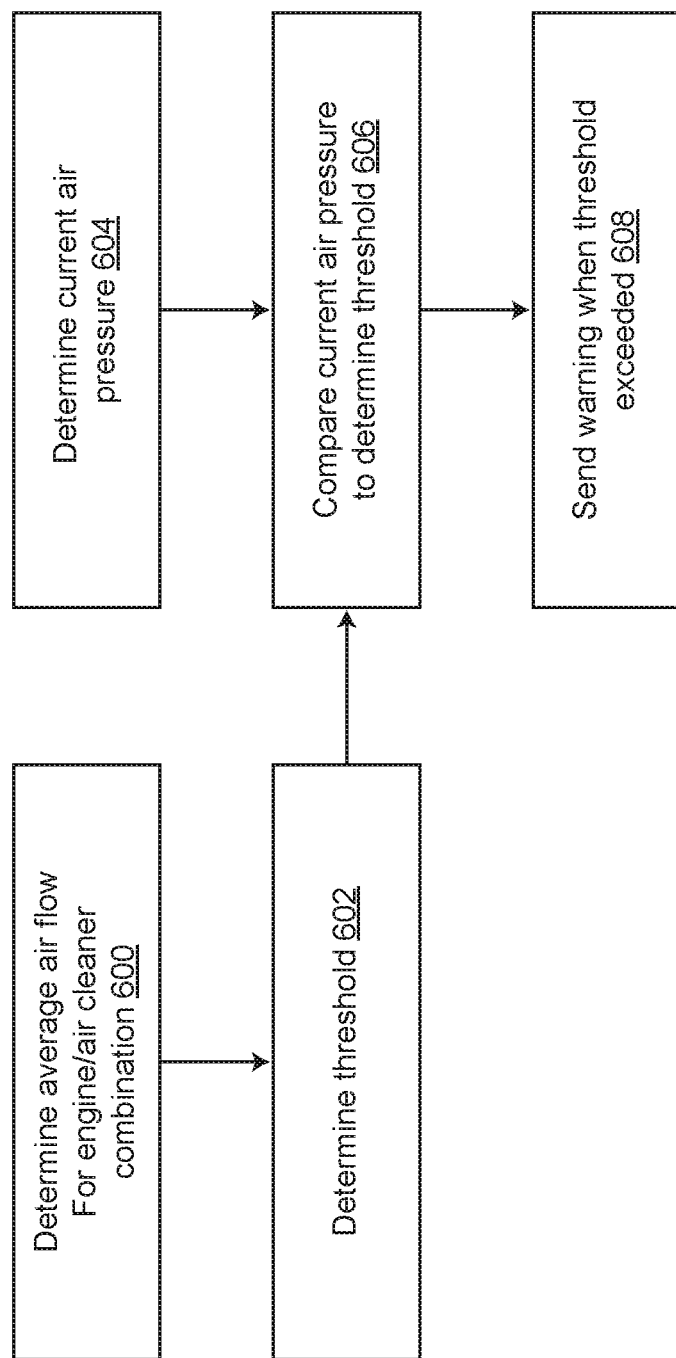
FIG. 6 is a flowchart of an example process to monitor air cleaner health.

FIG. 6 is a flowchart of an example process to track/monitor air cleaner health. On an EFI system that sends both a TPS sensor 32 signal and a manifold air pressure (MAP) sensor 66 signal, the EGU 24 can compare the two sensors 32, 66 signals over time to assess the health of the air cleaner 62. When an engine 20 is new and the engine 20 reached high load and high RPM conditions, the MAP sensor 66 signal can be learned as the baseline air cleaner flow. As the air cleaner 62 clogs with dirt, the MAP sensor 66 signal degrades, since at the same RPM and throttle opening the air cleaner 62 flows less air from the added restriction. The EGU 24 can determine a threshold and store the threshold that characterizes a significantly clogged air filter. The characteristic value can also be compensated for barometric pressure changes to reduce false readings.

An air inlet of the engine 20 can be provided with an air cleaner to maintain a cleanliness of the air to the engine 20. As the air cleaner becomes dirty and clogs, the EGU 24 determines when the old, dirty air cleaner needs to be changed to a new air cleaner. In one example, a baseline value for the high RPM and high load pressure is averaged and recorded, and set over the first x hours of engine operation, e.g., about 10 hours, representing the average air flow recorded in the cell, e.g., based on a correction factor, an air flow calculation and/or the raw MAP sensor 66 signal. The average flow can vary for different air cleaner models and engines. By taking the average over the first x hours of the engine 20, different manufacturers can select their own air cleaner models to use, and each EGU 24 learns its own baseline for the engine/air cleaner combination (600).

The current air pressures for the engine 20 can be monitored and recorded by the EGU 24, and compared with a threshold to determine an amount of air flow restriction, and if the air cleaner needs to be replaced, e.g., because the air cleaner is too dirty (602). The thresholds can be determined by recording an air flow, using information from throttle angle sensor 32 and absolute manifold air pressure sensors 66, to represent high RPM and high load. The EGU 24 can also store air pressure thresholds for different throttle positions in memory 25. As engine hours accumulate (604), the EGU 24 compares the current value to the original set value (606) to provide a calibrateable trigger value that can be used as the threshold. When the current value exceeds this trigger value a "restricted air filter" message can be recorded. The warning message can be displayed through a service software/CAN interface, and/or flashing the MIL at a low frequency, to indicate that it is time to replace the current air cleaner with a new air cleaner (608).

For load anticipation, the EGU 24 can monitor the CAN bus 70 for a power takeoff (PTO) engage signal 68 and modify operating parameters of the engine 20 in advance of the load being applied to a crankshaft of the engine 20. The PTO engage signal 68 can raise a software flag for an algorithm of the EGU 24 to modify speed set-point, fueling, spark and/or throttle position parameters to prepare the engine 20 for load pickup. The programmable parameters are available in a calibratable ramp format in the time domain. The EGU 24 can change the speed set-point to a value different than the throttle request once the load engage ramp has been completed, and can bypass the calibrator, if needed. The load anticipation flag is automatically reset once a successful load engage event has been identified or with a calibratable countdown timer variable. The EGU 24 can use a secondary flag to notify the system of PTO disengage with similar calibratable ramps for the parameters and the ability to follow the throttle request as normal.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it is appreciated that different combinations of elements and/or functions may be provided by alternative embodiments without departing from the scope of the disclosure and the appended claims.

The systems, methods and logic described above may be implemented in many different ways in many different combinations of hardware, software, firmware, or any combination thereof. In one example, the systems, methods and/or logic can be implemented with a processor and a memory, where the memory stores instructions, which when executed by the processor, causes the processor to perform the systems and methods. The processor may mean any type of circuit such as, but not limited to, a microprocessor, a microcontroller, a graphics processor, a digital signal processor, or another processor. The processor may also be implemented with discrete logic or components, or a combination of other types of analog or digital circuitry, combined on a single integrated circuit or distributed among multiple integrated circuits. All or part of the logic described above may be implemented as instructions for execution by the processor, controller, or other processing device and may be stored in a tangible or non-transitory machine-readable or computer-readable medium such as flash memory, random access memory (RAM) or read only memory (ROM), erasable programmable read only memory (EPROM) or other machine-readable medium such as a compact disc read only memory (CDROM), or magnetic or optical disk. A product, such as a computer program product, may include a storage medium and computer readable instructions stored on the medium, which when executed in an endpoint, computer system, or other device, cause the device to perform operations according to any of the description above. The memory can be implemented with one or more hard drives, and/or one or more drives that handle removable media, such as diskettes, compact disks (CDs), digital video disks (DVDs), flash memory keys, and other removable media.

The processing capability of the system may be distributed among multiple system components, such as among multiple processors and memories, optionally including multiple distributed processing systems. Parameters, databases, and other data structures may be separately stored and managed, may be incorporated into a single memory or database, may be logically and physically organized in many different ways, and may implemented in many ways, including data structures such as linked lists, hash tables, or implicit storage mechanisms. Programs may be parts (e.g., subroutines) of a single program, separate programs, distributed across several memories and processors, or implemented in many different ways, such as in a library, such as a shared library (e.g., a dynamic link library (DLL)). The DLL, for example, may store code that performs any of the system processing described above.

Many modifications and other embodiments set forth herein will come to mind to one skilled in the art having the benefit of the teachings presented in the foregoing descriptions and the associated drawings. Although specific terms are employed herein, they are used in a generic and descriptive sense only and not for purposes of limitation.

We claim:

1. A system for tracking health of an air cleaner of an engine comprising:
    an air manifold through which air passes in route to the engine;
    an air cleaner through which air passes in route to the engine;
    at least one sensor;
    an electronic governor control unit in communication with the at least one sensor, wherein the electronic governor control unit is configured to receive at least one signal from the at least one sensor, to determine a threshold based on the at least one signal, and to average, record, and set over a first pre-determined number of hours of engine operation an average air flow;
    an air pressure sensor configured to sense an air pressure in the manifold after the threshold has been determined and to generate a corresponding air pressure signal, wherein the electronic governor control unit is configured to receive the corresponding air pressure signal and to compare the corresponding air pressure signal to the threshold; and
    wherein the electronic governor control unit is further configured to send a warning signal when the threshold has been exceeded.

2. The system of claim 1, wherein the at least one sensor comprises the air pressure sensor.

3. The system of claim 1 further comprising a throttle, wherein the at least one sensor comprises a throttle position sensor configured to generate a throttle position signal based on a position of the throttle.

4. The system of claim 3, wherein the at least one sensor further comprises the air pressure sensor.

5. The system of claim 1, wherein the electronic governor control unit is configured to learn a baseline for the engine and the air cleaner based on the average air flow.

6. The system of claim 1, wherein the electronic governor control unit is configured to determine the average air flow based on a correction factor.

7. The system of claim 1, wherein the electronic governor control unit is configured to determine the average air flow based on an air flow calculation.

8. The system of claim 1, wherein the electronic governor control unit is configured to determine the average air flow based on the corresponding air pressure signal.

9. A system for tracking health of an air cleaner of an engine comprising:
- an air manifold through which air passes in route to the engine;
- an air cleaner through which air passes in route to the engine;
- at least one sensor;
- an electronic governor control unit in communication with the at least one sensor, wherein the electronic governor control unit is configured to receive at least one signal from the at least one sensor, wherein the electronic governor control unit is configured to average, record, and set over a first pre-determined number of hours of engine operation an average air flow, and wherein the electronic governor control unit is configured to determine a threshold based on the at least one signal;
- an air pressure sensor configured to sense an air pressure in the manifold after the threshold has been determined and to generate a corresponding air pressure signal, wherein the electronic governor control unit is configured to receive the corresponding air pressure signal and to compare the corresponding air pressure signal to the threshold; and
- wherein the electronic governor control unit is further configured to send a warning signal when the threshold has been exceeded.

10. The system of claim 9, wherein the at least one sensor comprises the air pressure sensor.

11. The system of claim 9 further comprising a throttle, wherein the at least one sensor comprises a throttle position sensor configured to generate a throttle position signal based on a position of the throttle.

12. The system of claim 11, wherein the at least one sensor further comprises the air pressure sensor.

13. The system of claim 9, wherein the electronic governor control unit is configured to learn a baseline for the engine and the air cleaner based on the average air flow.

14. The system of claim 9, wherein the electronic governor control unit is configured to determine the average air flow based on a correction factor.

15. The system of claim 9, wherein the electronic governor control unit is configured to determine the average air flow based on an air flow calculation.

16. The system of claim 9, wherein the electronic governor control unit is configured to determine the average air flow based on the corresponding air pressure signal.

* * * * *